(12) United States Patent
Dedick et al.

(10) Patent No.: US 11,959,384 B1
(45) Date of Patent: Apr. 16, 2024

(54) ELECTRICAL POWER GENERATION USING STRUCTURALLY ALTERED GAS MOLECULES

(71) Applicants: H2Plus LLC, San Diego, CA (US); H2Plus Operations, LLC, San Diego, CA (US)

(72) Inventors: Gene Dedick, Grand Junction, CO (US); Jared Roberts, Grand Junction, CO (US)

(73) Assignees: H2Plus LLC, San Diego, CA (US); H2Plus Operations, LLC, San Diego, CA (US)

( * ) Notice: Subject to any disclaimer, the term of this patent is extended or adjusted under 35 U.S.C. 154(b) by 0 days.

(21) Appl. No.: 18/376,783

(22) Filed: Oct. 4, 2023

Related U.S. Application Data

(63) Continuation-in-part of application No. PCT/US2022/044167, filed on Sep. 21, 2022, which is a continuation of application No. 17/487,613, filed on Sep. 28, 2021, now Pat. No. 11,384,440, application No. 18/376,783, filed on Oct. 4, 2023 is a continuation-in-part of application No. PCT/US2022/044168, filed on Sep. 21, 2022, which is a continuation of application No. 17/743,632, filed on May 13, 2022, now Pat. No. 11,634,823, which is a continuation of application No. 17/487,613, filed on Sep. 28, 2021, now Pat. No. 11,384,440, said
(Continued)

(51) Int. Cl.
*C25B 1/04* (2021.01)
*C25B 15/08* (2006.01)
*F01D 15/10* (2006.01)
*F02C 7/22* (2006.01)
*F02C 9/40* (2006.01)

(52) U.S. Cl.
CPC ............... *F01D 15/10* (2013.01); *C25B 1/04* (2013.01); *C25B 15/081* (2021.01); *F02C 7/22* (2013.01); *F02C 9/40* (2013.01); *F05B 2220/702* (2013.01)

(58) Field of Classification Search
CPC .......... C25B 1/04; C25B 15/027; B01J 19/12; C01B 5/00
See application file for complete search history.

(56) References Cited

U.S. PATENT DOCUMENTS

| | | |
|---|---|---|
| 11,384,440 B1 | 7/2022 | Roberts et al. |
| 11,634,823 B2 | 4/2023 | Roberts et al. |
| 2022/0220621 A1* | 7/2022 | Morrison .................. B64F 1/28 |

* cited by examiner

*Primary Examiner* — Zulmariam Mendez
(74) *Attorney, Agent, or Firm* — Georgiy L. Khayet

(57) ABSTRACT

Systems and methods for power generation are provided. An example method includes pretreating water by a water pretreatment system to obtain purified water, providing the purified water to a chemical reaction chamber containing a catalyst, applying a focused magnetic field and an electric field to a mixture of the purified water and the catalyst to cause generation of structurally altered gas molecules from the purified water, wherein the structurally altered gas molecules are a combination of two parts hydrogen and one part oxygen and the structurally altered gas molecule has a hydrogen-oxygen-hydrogen bond angle between 94 degrees and 104 degrees and a hydrogen-oxygen bond length between 0.95 Angstrom and 1.3 Angstrom, and providing the structurally altered gas molecules to a turbine, wherein the turbine combusts gas includes the structurally altered gas molecules to drive a turbine generator in order to generate electrical power.

20 Claims, 13 Drawing Sheets

Related U.S. Application Data application No. PCT/US2022/044168 is a continuation of application No. 17/487,613, filed on Sep. 28, 2021, now Pat. No. 11,384,440.

| Sample | Total Heat of Combustion (Cal) | Pressure of Gas in Bomb (psi) | Heat of Combustion (Cal/psi) | Avg. Heat of Combustion (Cal/psi) | Avg. Heat of Combustion (kJ/g) | Energy Increase (kJ/g) (%) |
|---|---|---|---|---|---|---|
| Hydrogen | 1074 | 25 | 43.0 | 44.0 | 0.184 | - |
|  | 1799 | 40 | 45.0 |  |  |  |
| H2PLUS Gas | 572 | 10 | 57.2 | 53.3 | 0.223 | 21.2% |
|  | 510 | 10 | 51.0 |  |  |  |
|  | 773 | 14 | 55.2 |  |  |  |
|  | 746 | 15 | 49.8 |  |  |  |

FIG. 3

| Components | Mol % | Wt. % | at 14.696 psia |
|---|---|---|---|
| Hydrogen | 67 | 11.3 | |
| Oxygen | 33 | 88.7 | |
| Helium | NIL | NIL | |
| Carbon Monoxide | NIL | NIL | |
| Carbon Dioxide | NIL | NIL | |
| Sulfur | NIL | NIL | |
| Nitrogen | NIL | NIL | |
| Methane | NIL | NIL | |
| Ethane | NIL | NIL | |
| Ethylene | NIL | NIL | |
| Propane | NIL | NIL | |
| Propylene | NIL | NIL | |
| ISO-Butane | NIL | NIL | |
| n-Butane | NIL | NIL | |
| Propadiene | NIL | NIL | |
| Trans-2-Butene | NIL | NIL | |
| 1-Butene | NIL | NIL | |
| ISO-Butylene | NIL | NIL | |
| CIS-2-Butene | NIL | NIL | |
| NEO Pentane | NIL | NIL | |
| ISO-Pentane | NIL | NIL | |
| n-Pentane | NIL | NIL | |
| 1,3 Butadiene | NIL | NIL | |
| Hexanes Plus | NIL | NIL | |

FIG. 4

Comparable Gas Specifications 500

| | NATURAL GAS | HYDROGEN | GAS |
|---|---|---|---|
| | 502 | 504 | 506 |
| HHV MJ/kg | 52.20 | 141.70 | 172.87 |
| Energy Density (MJ*Kg/SM3) | 37.43 | 12.75 | 89.03 |
| Atomic Mass (g/mol) | 16.04 | 1.01 | 12.16 |
| Density (Kg/SM3) | 0.72 | 0.09 | 0.52 |
| HHV (MJ/M3 at 200 bar) | 39.76 | 12.76 | 97.93 |
| Volume (AMU/Density at SM3) (SM3 at 1.01325 bar, 15C) | 22.37 (14.696 psig) | 11.20 | 23.61 |
| Liquid to Gas volume ratio | 600 | 848 | 2200 |

FIG. 5

ELECTRICAL POWER GENERATION USING STRUCTURALLY ALTERED GAS MOLECULES

CROSS-REFERENCE TO RELATED APPLICATIONS

This application is a Continuation-in-Part of PCT Application No. PCT/US22/44167 filed on Sep. 21, 2022, and entitled "STRUCTURALLY ALTERED GAS MOLECULE PRODUCED FROM WATER AND METHOD OF GENERATION THEREOF," which claims benefit of and priority of U.S. patent application Ser. No. 17/487,613 filed on Sep. 28, 2021, and entitled "STRUCTURALLY ALTERED GAS MOLECULE PRODUCED FROM WATER AND METHOD OF GENERATION THEREOF." This application is a Continuation-in-Part of PCT Application No. PCT/US22/44168 filed on Sep. 21, 2022, and entitled "STRUCTURALLY ALTERED GAS MOLECULE PRODUCED FROM WATER AND METHOD OF GENERATION THEREOF," which claims benefit of and priority of U.S. patent application Ser. No. 17/487,613 filed on Sep. 28, 2021, and entitled "STRUCTURALLY ALTERED GAS MOLECULE PRODUCED FROM WATER AND METHOD OF GENERATION THEREOF," and claims benefit of and priority of U.S. patent application Ser. No. 17/743,632 filed on May 13, 2022, and entitled "STRUCTURALLY ALTERED GAS MOLECULE PRODUCED FROM WATER AND METHOD OF GENERATION THEREOF." The subject matter of the aforementioned applications is incorporated herein by reference in its entirety.

TECHNICAL FIELD

This disclosure relates to methods and systems for generation of electric power using structurally altered gas molecules.

BACKGROUND

In recent years, environmental and government agencies have urged the energy sector to move away from fossil fuels to alternative fuels sources. One of these alternatives is hydrogen production and combustion of the hydrogen in turbine generators, fuel cells, as well as in hydrogen burning engines. Hydrogen is the most basic and most common element on Earth. Hydrogen ($H_2$) is a gas that combines with oxygen to make water ($H_2O$), and with carbon to form compounds such as methane and coal. Hydrogen is also a potential source of clean energy. In fact, hydrogen has the highest energy content of any fuel used today.

Hydrogen does not occur naturally in a gaseous form on Earth but can be produced. Use of hydrogen energy is not harmful to the environment because only water and heat are released as byproducts when burning the hydrogen. However, the process used for production of hydrogen is not as environmentally friendly. To produce usable hydrogen, it has to be separated from water, biomass (plant and animal waste), coal, or natural gas. About 95% of the hydrogen used today is produced by a process called steam reforming, which is separating hydrogen atoms from carbon atoms in methane. This process releases greenhouse gases or carbon dioxide equivalent ($CO_2e$) into the atmosphere. Electrolysis, the other production method, separates hydrogen from water. Electrolysis can be powered by renewable energy such as wind, hydropower and solar energy, in order to eliminate emissions. The downside of electrolysis is its cost. Therefore, for hydrogen to reach its full potential as an energy source, inexpensive methods of production from clean, renewable sources need to be developed.

Currently, there are various types of hydrogen used in power generation.

Grey hydrogen: obtained by steam methane reforming and the $CO_2$ produced and released into the atmosphere.

Blue hydrogen: obtained by steam methane reforming but the $CO_2$ is captured and stored in a Carbon Capture, Utilization and Storage (CCUS) system.

Green hydrogen: obtained by electrolysis of water (or steam) using electricity obtained from a renewable source such as wind or solar.

Brown hydrogen: produced by the gasification of coal, generating $CO_2$ emissions in the process.

Thus, there is a need for fuel alternatives that can be produced and utilized to generate electrical power without $CO_2$ emission.

SUMMARY

This summary is provided to introduce a selection of concepts in a simplified form that are further described in the Detailed Description below. This summary is not intended to identify key features or essential features of the claimed subject matter, nor is it intended to be used as an aid in determining the scope of the claimed subject matter.

According to one example embodiment of the present disclosure, a method for generating power is provided. The method may include pretreating water by a water pretreatment system to obtain purified water. The method may include providing the purified water to a chemical reaction chamber containing a catalyst. The method may allow applying a focused magnetic field and an electric field to a mixture of the purified water and the catalyst to cause generation of structurally altered gas molecules from the purified water. The structurally altered gas molecules are a combination of two parts hydrogen and one part oxygen. The structurally altered gas molecule has a hydrogen-oxygen-hydrogen bond angle between 94 degrees and 104 degrees and a hydrogen-oxygen bond length between 0.95 Angstrom and 1.3 Angstrom. The method may include providing structurally altered gas molecules to a turbine. The turbine may combust gas including the structurally altered gas molecules to drive a turbine to generate electrical power.

Other example embodiments of the disclosure and aspects will become apparent from the following description taken in conjunction with the following drawings.

BRIEF DESCRIPTION OF THE SEVERAL VIEWS OF THE DRAWINGS

Exemplary embodiments are illustrated by way of example and not limitation in the figures of the accompanying drawings, in which like references indicate similar elements.

FIG. 3 shows a table illustrating calorimetry test results in a bomb calorimetry experiment.

FIG. 4 is a table illustrating results of a test for analysis of gas using gas chromatography, according to the present disclosure.

FIG. 5 is a table illustrating characteristics of natural gas, hydrogen, and gas including structurally altered gas molecules of the present disclosure.

DETAILED DESCRIPTION

Figure 1:
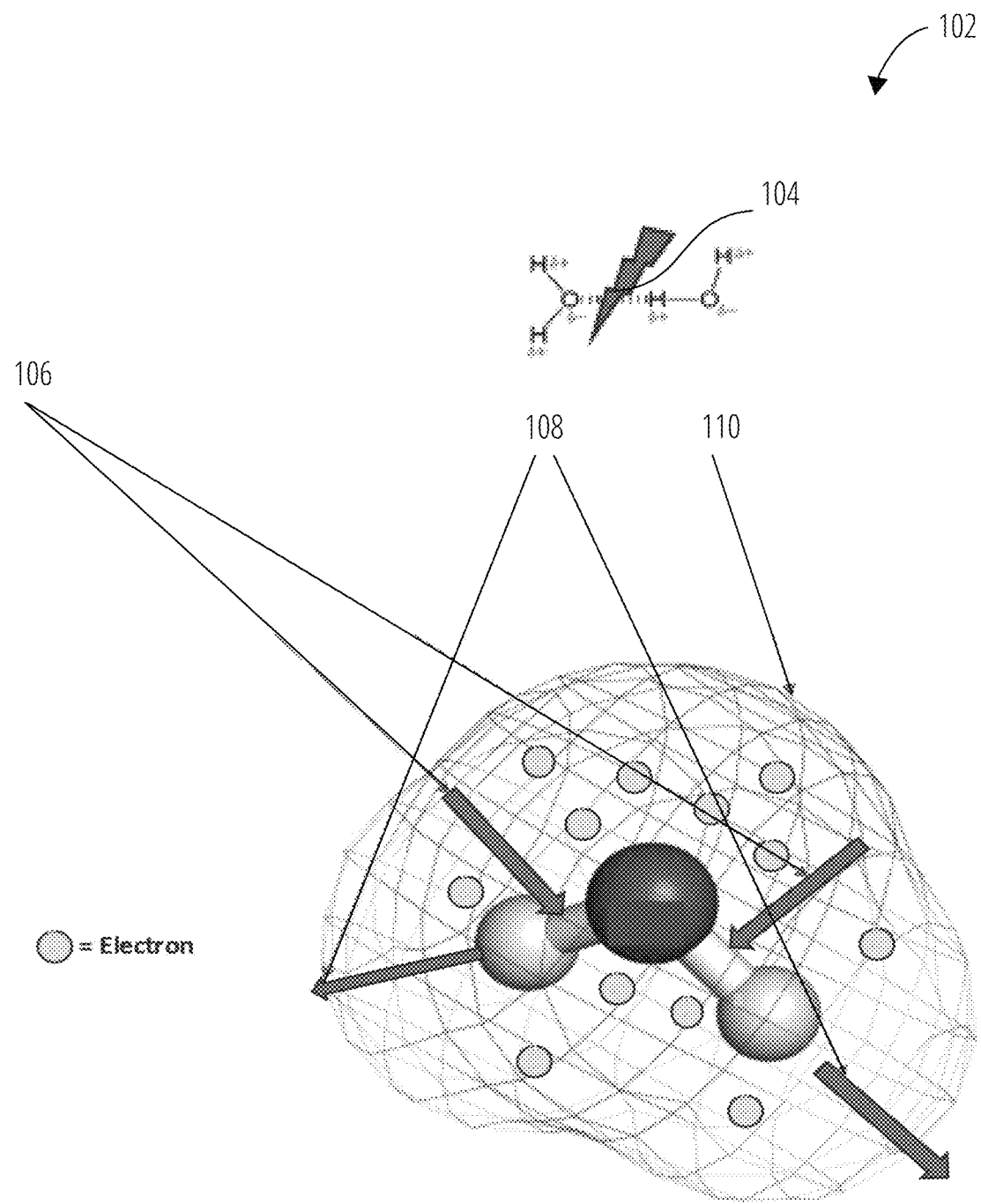
FIG. 1 shows a structurally altered gas molecule deployed in the method for generating power, according to some embodiments of the present disclosure.

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical, and operational changes can be made without departing from the scope of what is claimed. The following detailed description is, therefore, not to be taken in a limiting sense, and the scope is defined by the appended claims and their equivalents.

Generally, the embodiments of this disclosure relate to methods for generation and deployment of structurally altered gas molecules derived from water. The generation of the structurally altered gas molecules is performed in a chemical reaction chamber that may accommodate compound mixtures in solid, liquid, gas, or multi-phase form. The chemical reaction chamber may have a specific geometric electromagnetic field configuration to attract hydrated and/or conventional electrons into the adjacent areas of the water molecules without a chemical reaction occurring between the water molecules.

The method according to the present disclosure results in creating a water molecule with special characteristics by treatment of water into the chemical reaction chamber. The chemical reaction chamber may be characterized by two configurations. First, the chemical reaction chamber enables the introduction of a compound mixture, which may be in solid, liquid, gas, or multi-phase form, the purpose of which is to support or enhance electromagnetic field and which specifically does not have any chemical interaction with the water. Second, the chemical reaction chamber enables the introduction of energy in a geometrically configured manner, in which the result of the treatment of the water molecules is to render the water molecule as having a greater probability to attract hydrated and/or conventional electrons into the adjacent areas of the water molecules, without a chemical reaction between the water molecule and electrons.

In the chemical reaction chamber, for a period after the treatment of the water molecules, the electron attracting water molecules can be introduced into an environment where a separate chemical, non-chemical, or hybrid process is occurring and where heightened hydrated and/or conventional electron availability (either accepting or donating) may be useful in allowing and/or enhancing the productivity of such process. Either organically, such as the water molecule's advantage in electron transport in the mitochondria, or in various inorganic processes, such as, for example, the production of hydrogen or the reduction of carbon dioxide equivalent ($CO_2e$).

The gas including the structurally altered gas molecules can be deployed directly into various processes that use electrons and the molecule itself for any process that requires them. The applications of the above process may include but are not limited to fossil hydrogen turbines, hydrogen engines and hydrogen fuel cells to generate power, increase efficiency and reduce $CO_2e$ emissions to the environment from these and other hydrogen combustion systems.

Referring now to the drawings, various embodiments are described in which like reference numerals represent like parts and assemblies throughout the several views. It should be noted that the reference to various embodiments does not limit the scope of the claims attached hereto. Additionally, any examples outlined in this specification are not intended to be limiting and merely set forth some of the many possible embodiments for the appended claims.

This application makes reference to U.S. patent application Ser. No. 17/487,613, filed on Sep. 28, 2021, now U.S. Pat. No. 11,384,440, and to U.S. patent application Ser. No. 17/743,632, filed on May 13, 2022, now U.S. Pat. No. 11,634,823, the subject matter of which is incorporated herein by reference in its entirety for all purposes. Processes and systems described herein may be better understood in light of the concepts found in these references.

FIG. 1 shows a structurally altered gas molecule 102 deployed in the method for generating power, according to some embodiments of the present disclosure. The structurally altered gas molecules 102 can be derived from water. The structurally altered gas molecule can be generated by processes described in U.S. Pat. Nos. 11,384,440 and 11,634,823.

In structurally altered gas molecule 102, hydrogen bonds 104 are broken to allow a gaseous single molecule form of water to exist and enable the following adjustments: 1) a bond angle 106 is decreased; 2) oxygen-hydrogen covalent bond length 108 is increased; 3) adjustments allow room for more electrons in probability spheres 110. Per the molecular orbital theory (MOT), small molecules like water can adjust electron energy levels around the probability spheres. The MOT states that not just the atoms themselves but the entire molecule shares electrons now.

As to the structurally altered gas molecule 102, the molecular alterations include lengthening of the H—O bonds from 0.95 Angstroms up to 1.3 Angstrom and decreasing the H—O—H bond angle from 104.5° to as small as 94°.

Thus, structurally altered gas molecule 102 is a molecule consisting of hydrogen and oxygen in a 2:1 ratio. However, the structurally altered gas molecule 102 is not a mixture of $H_2$ and $O_2$ gases. Neither the structurally altered gas molecule 102 is hydrogen peroxide or conventional pure water or water vapor. The structurally altered gas molecules 102 exists as a gas at standard temperature that can be pressured up to 3000 psig while maintaining its stability. structurally altered gas molecules 102 can be generated on board moving vehicles as it is used and can also be stored like other gaseous fuels. The structurally altered gas molecules 102 has no geographic limitations for production. The gas including the structurally altered gas molecules 102 was tested in multiply experiments. These experiments showed that generation of structurally altered gas molecules 102 is scalable, sustainable, and safe.

The structurally altered gas molecules 102 may be used in generation of energy alternative to hydrogen energy. The gas according to the present disclosure, i.e., the structurally altered gas molecules 102, provides 21.2% more energy in kJ/kg generated. At present, green hydrogen costs $1-$2 dollars per kilogram to manufacture. Blue hydrogen is $5-$7 per kilogram. The gas according to the present disclosure is $0.658 per kilogram. The gas according to the present disclosure requires no oxygen stripping process like grey, brown, green, blue hydrogen. The method according to the present disclosure generates NO $NO_x$, $SO_x$, or $CO_2$e. Nearly 100% of the burned fuel is captured and rejuvenated in system 202 (described in FIGS. 2A and 2B) compared to a conventional hydrogen burning system where the exhaust products are not captured and which are less efficient. The gas, according to the present disclosure, can be stored and transported or generated on board and used real-time. The gas, according to the present disclosure, provides no toxic exposure to operators or users. There are no toxins generated with the method according to the present disclosure. The raw materials for the gas (water) are collected and recycled indefinitely. The footprint for 100 MW plant for performing the method according to the present disclosure is 0.0098 sq km or 0.004 sq mi. Footprint for 100 MW hydrogen plant is 3× or more. The footprint for 100 MW wind farm is 25 sq km or 10 sq mile. Footprint for 100 MW solar panel field is 25 sq km or 10 sq mile.

Figure 2A:
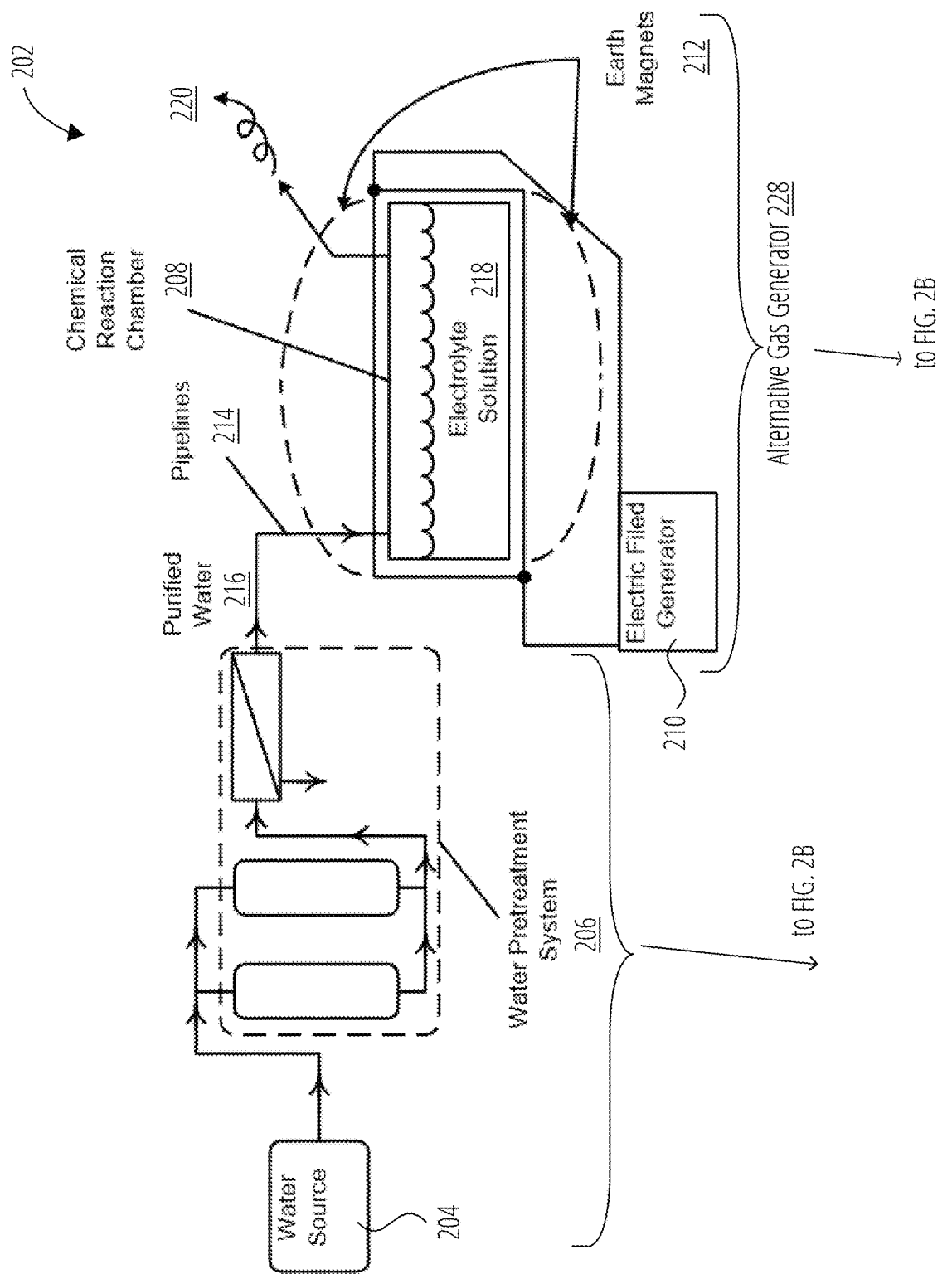
FIG. 2A and FIG. 2B show a system for generation of power, according to some embodiments of the present disclosure.
Figure 2B:
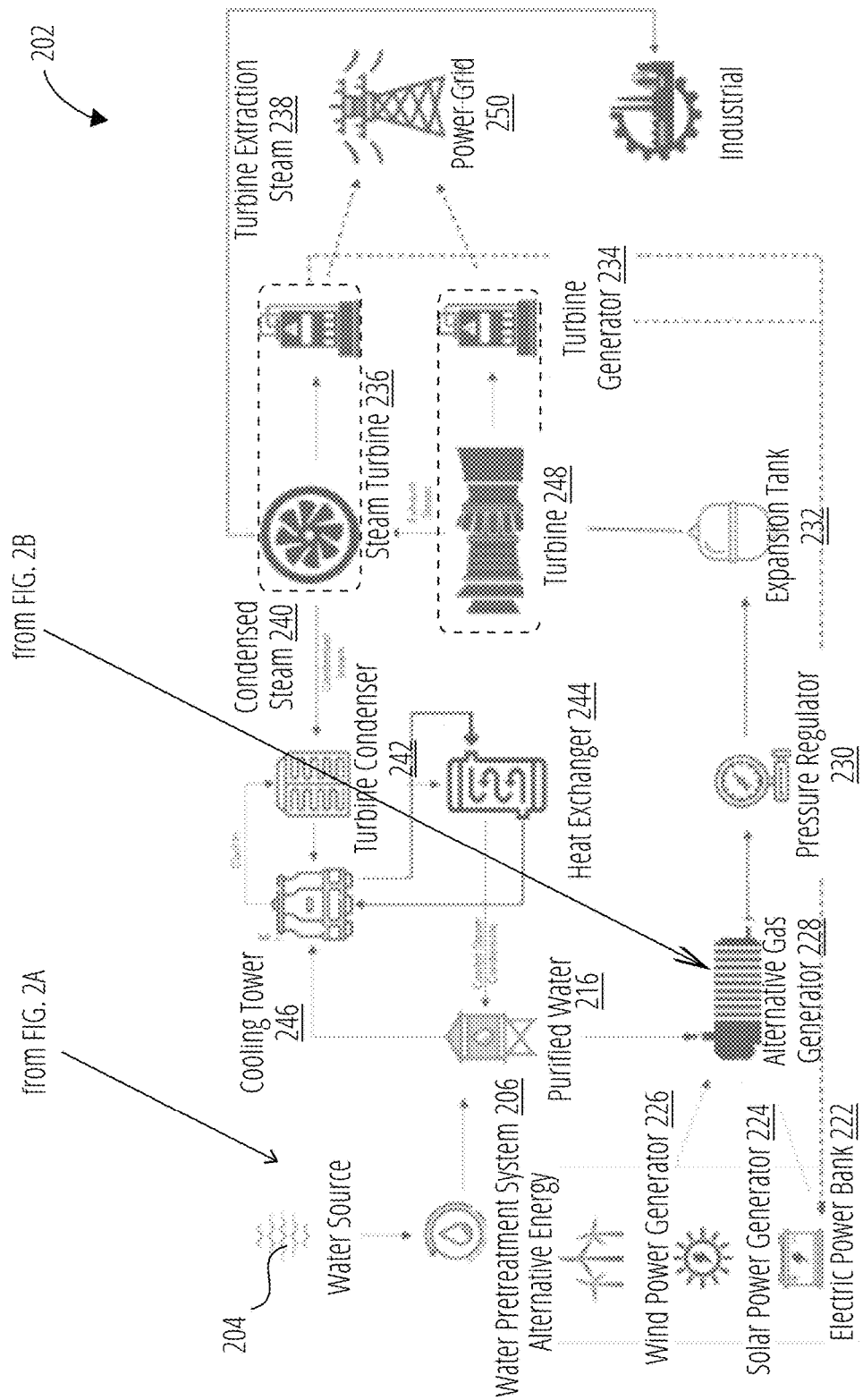

FIG. 2A and FIG. 2B show a system 202 for generation of power, according to some embodiments of the present disclosure. The system 202 may include a water source 204, a water pretreatment system 206, alternative gas generator 228, an electric power bank 222, a solar power generator 224, a wind power generator 226, an alternative gas generator 228, a pressure regulator 230, an expansion tank 232, a turbine 248, a turbine generator 234, a steam turbine 236, a turbine extraction steam 238, a turbine condenser 242, a heat exchanger 244, and a cooling tower 246. The alternative gas generator 228 may include a chemical reaction chamber 208, an electric field generator 210, a magnetic field generator such as earth magnets 212, and pipelines 214. In an example embodiment, the magnetic field generator may include one of the following: earth magnets, solenoids, electromagnets, and so forth.

Water source may provide water as a raw material for generating the gas molecule product. The water pretreatment system 206 may prepare the water for the chemical reaction chamber 208. The water pretreatment system 206 may include a filtration system, an absorption system, and a purification system to produce the purified water.

The chemical reaction chamber 208 may be configured to accommodate water and may contain an electrolyte solution 218. The electrolyte solution 218 can be made using a mixture of a hydroxide salt and acid salt. Purified water 216 can be provided to the chemical reaction chamber 208. The earth magnets 212 may generate a permanent focused magnetic field. The electric field generator 210 may generate an electric field. The focused magnetic field and the electrical field may drive a chemical reaction that generates the structurally altered gas molecule 220 from the purified water supplied into chemical reaction chamber 208. The electrolyte solution 218 may provide a medium for the focused magnetic field to align and impart energy of the focused magnetic field on the purified water mixed in with the electrolyte solution and, thereby, chemically generating the structurally altered gas molecule 102 from the purified water 216. The temperature in the chemical reaction chamber 208 can be from 60 degrees to 120 degrees Fahrenheit. The pressure in the chemical reaction chamber 208 can be from 1 atmosphere to 40 pounds per square inch gauge (psig). The structurally altered gas molecule 220 may have a higher probability of attraction of electrons into areas adjunct to the structurally altered gas molecule 220 than molecules of the water.

The structurally altered gas molecule 220 can be 99.9% hydrogen and oxygen combination in two parts of hydrogen to one part of oxygen ratio at the Standard Temperature of 68 degrees of Fahrenheit and pressure of 1 atmosphere (STP). The structurally altered gas molecule 220 may have the O—H bond length between 0.95 and 1.3 angstroms and the H—O—H bond angle between 94 degrees and 104 degrees.

The molecular weight of the structurally altered gas molecule 220 can be between 12.14 and 12.18 atomic mass units (AMUs) at STP. In comparison, the molecular weight of pure water vapor is 18 AMUs at STP. At STP, the relative density of the structurally altered gas molecule 220 compared to dry air is 41.18%-42.00%. In comparison, the relative density of pure water vapor compared to dry air is 62.19%. The structurally altered gas molecule 220 may remain stable at pressure of more than 300 psig.

When dissolved in pure water having 2 parts per million (ppm) of total dissolved solids (TDS) at 25 degrees of Celsius, the structurally altered gas molecule 220 may generate an ORP of approximately −50 to −360 mV and a pH of 6.1 to 6.8 in the resulting gas-water mixture. The ORP and pH may remain stable in a closed insoluble vessel for at least 30 days. In comparison, pure water does not possess a stable negative ORP at a pH below 7.

When dissolved in pure water (2 ppm TDS at 25 degrees Celsius), the structurally altered gas molecule 220 may reduce the concentration of TDS from 2.0 ppm to 1.0 ppm, i.e., the reduction is 50%. Barring contamination, the concentration of TDS remains stable at 1 ppm in a closed insoluble vessel indefinitely.

The changes in structure and properties of the structurally altered gas molecule 220 are caused by changes in electronic structure of the gas structurally altered structurally altered gas molecule 220 due to applying the focused magnetic field and the electrical field to the mixture of the electrolyte solution 218 and purified water 216.

The structurally altered gas molecule 220 may have a peak at 600 inverse centimeters in an infrared spectrum. When infused in water, the structurally altered gas molecule 220 may cause a hydrogen bonding in the water to be neutralized.

Referring now to FIG. 2B, after being generated, the structurally altered gas molecules can be provided, vi pressure regulator 230 and expansion tank 232, to turbine generator 234. Turbine 248 combusts gas including the structurally altered gas molecules to drive turbine generator 234 to generate electrical power. Electrical power can be provided to power grid 250.

The water pretreatment system 206 and alternative gas generator 228 can be powered by wind power generator 226 and solar power generator 224. In certain embodiments, the power produced by wind power generator 226 or solar power generator 224 can be stored electric power bank 222. The electric power bank 222 can provide power to both water pretreatment system 206 and alternative gas generator 228.

Steam produced by turbine 248 can be provided to a steam turbine 236 designed to produce further electrical power. Condensed steam 240 produced by steam turbine 236 can be processed by turbine condenser 242, heat exchanger 244, and cooling tower 246 to generate cooled water that can be provided to as purified water 216 to alternative gas generator 228, where the alternative gas generator 228 generates structurally altered gas molecules 220.

Thus, system 202 can be used to generate power using structurally altered gas molecules 102. The power generation may include the following steps.

STEP 1: City water, well water, river water or trucked in water is sourced and pumped to the water pretreatment system 206. Once system 202 receives an initial fill of treated water, the further need for water is negligible because the system 202 is a closed loop that generates Blue Energy.

STEP 2: Water is pretreated to a specific quality with water pretreatment system 206, which can be a conventional pretreatment system similar to those used in power generation plants at present. The purified water 216 can be passed to a storage tank that supplies the purified water 216 to the alternative gas generator 228. It should be noted that more than one alternative gas generator 228 (also referred herein to as cells) can be used in system 202.

STEP 3: The purified water 216 can be added to alternative gas generators 228 at a specified flow rate. The alternative gas generators 228 may contain a proprietary catalyst that works in concert with a targeted magnetic field and electric field to alter the physical and chemical structure of the purified water 216 as described in FIG. 2A. The most notable change is that this structurally altered water departs from the alternative gas generators 228 as a gas that holds its properties until combustion in the downstream turbine 248.

STEP 3a: Wind power generators 226 or solar power generators 224 can be used to generate the necessary electrical energy to power alternative gas generators 228. This electrical energy can be stored in a battery bank shown as electric power bank 222.

STEP 4: The gas including structurally altered gas molecules 220 can be provided from alternative gas generators 228 directly to turbine 248. Turbine 248 provides the necessary combustion energy to drive the turbine generator 234 that generates electrical power for industry, institutions, government, private sector, and residential users. The exhaust from turbine 248 is pure steam. This steam can be sent directly to downstream extraction/condensing steam turbine 236 for additional electrical generation to power alternative gas generators 228.

STEP 5: The exhaust steam and or condensed steam from downstream extracting/condensing steam turbine 236 can be captured and cooled by a conventional condenser that can be water or air cooled. The cooled condensate can be pumped back to the same storage tank that supplies the water to the alternative gas generators 228.

In the process described in above steps 1-5, no $CO_{2e}$, $NO_x$, $SO_x$ or toxins are released to the environment.

FIG. 3 shows a table 300 illustrating calorimetry test results in a bomb calorimetry experiment to confirm higher energy in kJ per kg. The heat of combustion was measured using a modified American Society for Testing and Materials (ASTM) D240 procedure which enables the combustion of gases rather than of liquids or solids as is normally the case. For hydrogen 302, oxygen was supplied in stoichiometric excess. For the gas 304 of the present disclosure, no additional oxygen or air was supplied. In each test, the vessel was filled with sample gas twice, released to remove any residual air, and refilled a third time.

FIG. 4 is table 400 illustrating results of the standard ASTM D 1945 test for analysis of the gas according to the present disclosure by gas chromatography.

FIG. 5 is a table 500 illustrating characteristics of natural gas 502, hydrogen 504, and gas 506 including structurally altered gas molecules of the present disclosure. According to the tests, the structurally altered gas molecule is a molecule consisting of hydrogen and oxygen in a 2:1 ratio. It is not a mixture of $H_2$ and $O_2$ gases and not hydrogen peroxide or conventional pure water or water vapor. The structurally altered gas molecule exists as a gas at standard temperature that can be pressured up to 300 psig, while maintaining its stability. The structurally altered gas molecule has no geographic limitations for production. Unlike hydrogen, the structurally altered gas molecule does not back propagate, however, like for all fuels a certain pressure has to be maintained. The structurally altered gas molecule can be generated as it is used and can be stored like other gases used in combustion turbines. The structurally altered gas molecule creates a flame when it burns and does not create explosions like hydrogen. The generation of structurally altered gas molecules is scalable, sustainable, and safe.

Figure 6:
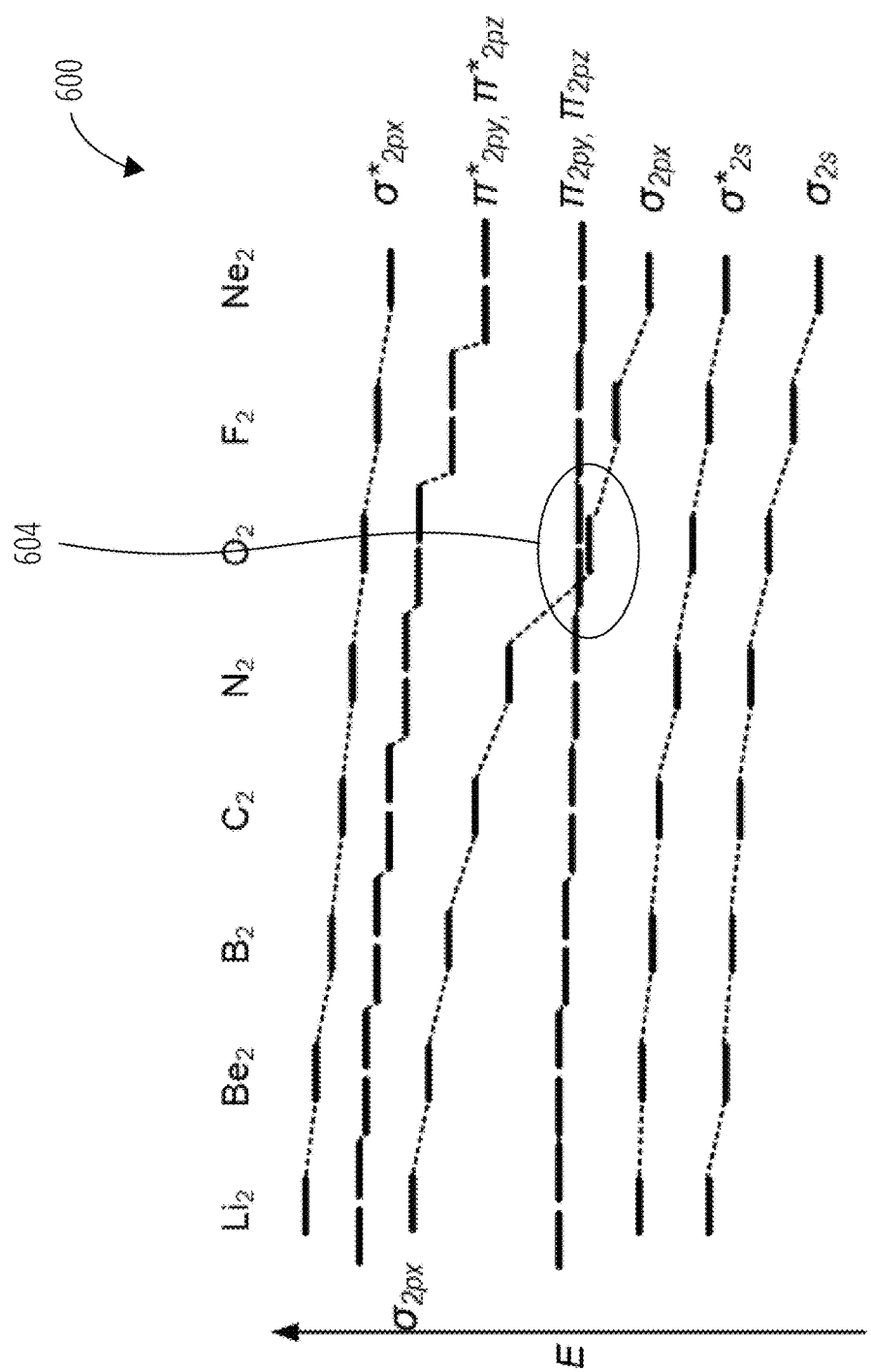
FIG. 6 is a diagram showing energy levels of molecular orbitals of homonuclear diatomic molecules of elements of the second period in the periodic table.

FIG. 6 is a diagram showing energy levels 600 of molecular orbitals of homonuclear diatomic molecules of elements of the second period in the periodic table. The gas according to the present disclosure has structural differences compared to divalent hydrogen, divalent oxygen, and pure water. The structural changes made to the gas according to the present disclosure include changes in the bond angle, bond length, and neutralization of the hydrogen bonding found in regular water. This is accomplished by imparting sufficient focused energy on regular water to overcome the collective bond energies mentioned above. Structural changes to allow molecules of the same outer valence orbitals with lone pairs of electrons in their structure (for example water) allow certain normally "liquid" molecules to exist as gases and at standard temperature and pressure after these said structural changes. These structural changes are observed in nature, and the phenomena is documented and taught in college chemistry curriculum as MOT.

In MOT, there is known a phenomenon called σ-π (sigma-pi) mixing. This phenomenon influences existing s and p molecular orbitals by imparting electromagnetic energy at the molecular level. In the case of oxygen, the sigma-2px, pi-2py and pi-2pz orbitals 604 are close enough to alter the respective stability at the molecular level. Thus, the energy levels of these orbitals can supersede each other with only small amounts of focused energy input. This superseding in the energy levels has a direct effect on the molecular wave function of a molecule, effective nuclear charge, atomic radius, and causes significant changes in the molecular structure.

Figure 7:
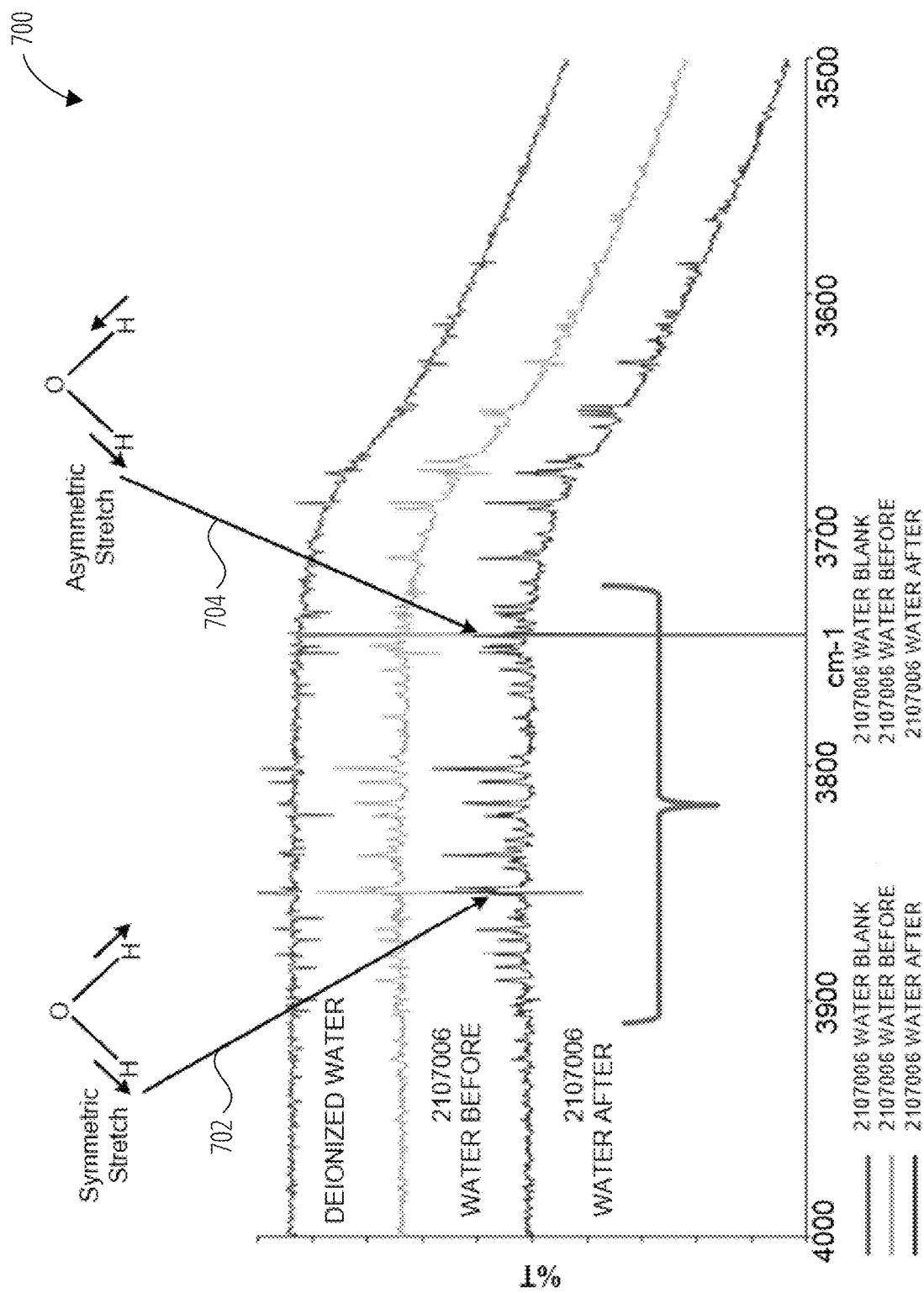
FIG. 7 is a plot of the Fourier Transform Infrared (FTIR) transmittance spectra of deionized water, pure water before being infused with the structurally altered gas molecules, and pure water after being infused with the structurally altered gas molecules.

FIG. 7 is a plot 700 of the Fourier Transform Infrared (FTIR) transmittance spectra of deionized water, a pure water before (WB) infusion with the structurally altered gas molecule, and a pure water after (WA) infusion with the structurally altered gas molecule in the region of 3500-4000 inverse centimeters ($cm^{-1}$).

Figure 8:
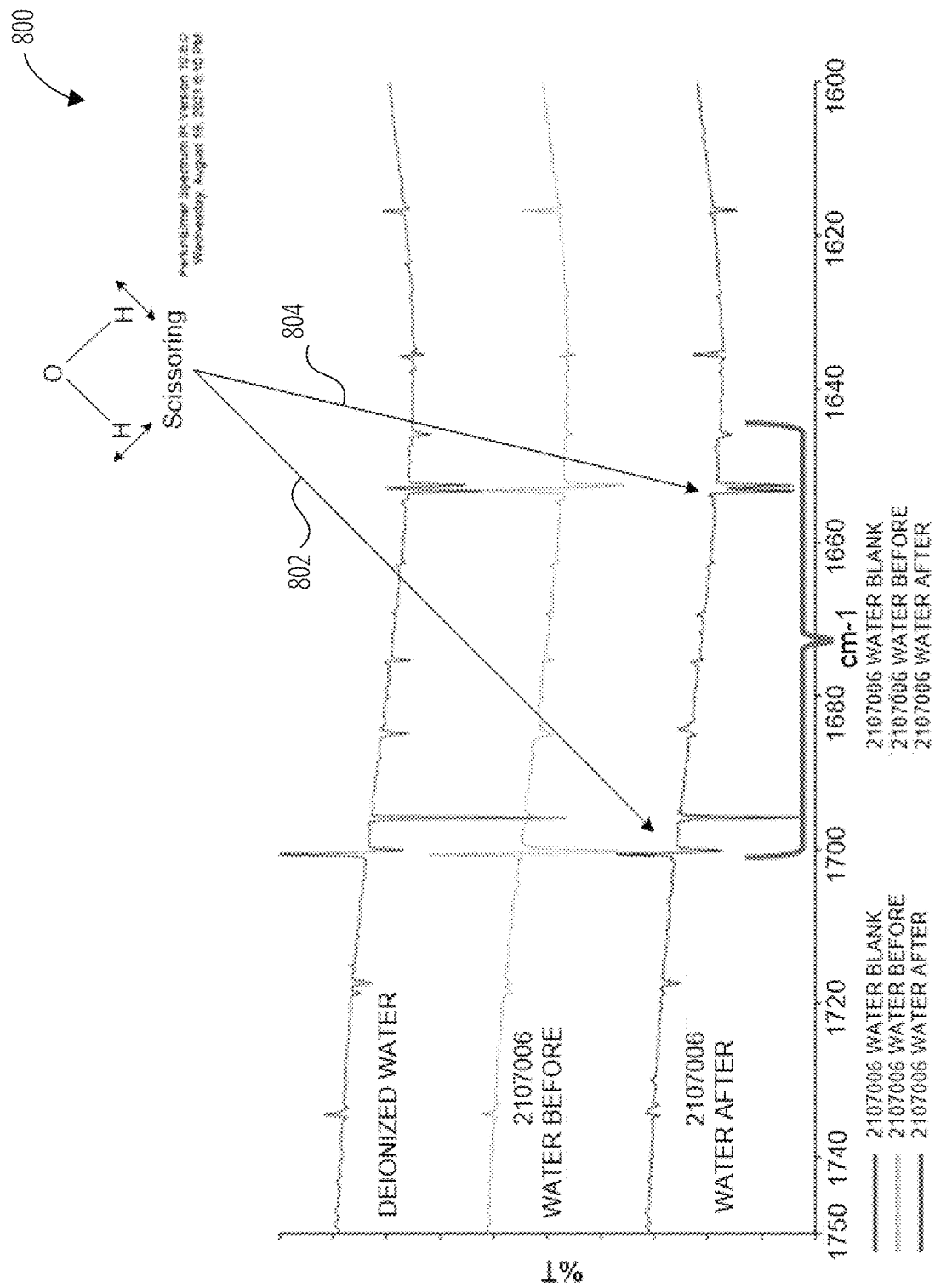
FIG. 8 is a plot of the FTIR transmittance spectra of pure water before being infused with the structurally altered gas molecules, and pure water after being infused with the structurally altered gas molecules in another region.

FIG. 8 is a plot 800 of the FTIR transmittance spectra of deionized water, WB, and WA in the region of 1600-1750 $cm^{-1}$. The plot 700 and plot 800 show differences in bands corresponding to the symmetrical and asymmetrical stretch in bond length and bands corresponding to the bond angle "scissoring".

FIG. 7 and FIG. 8 show the actual structural changes to the water molecule's bond length Stretch) and bond angle resulting from treatment by the gas according to the present disclosure. See changes referenced by arrow 702 and arrow 704 in FIG. 7 and arrow 802 and arrow 804 in FIG. 8 toward the changes in downward "dips" at specific transmittance (% T) and time interval ($cm^{-1}$).

Figure 9:
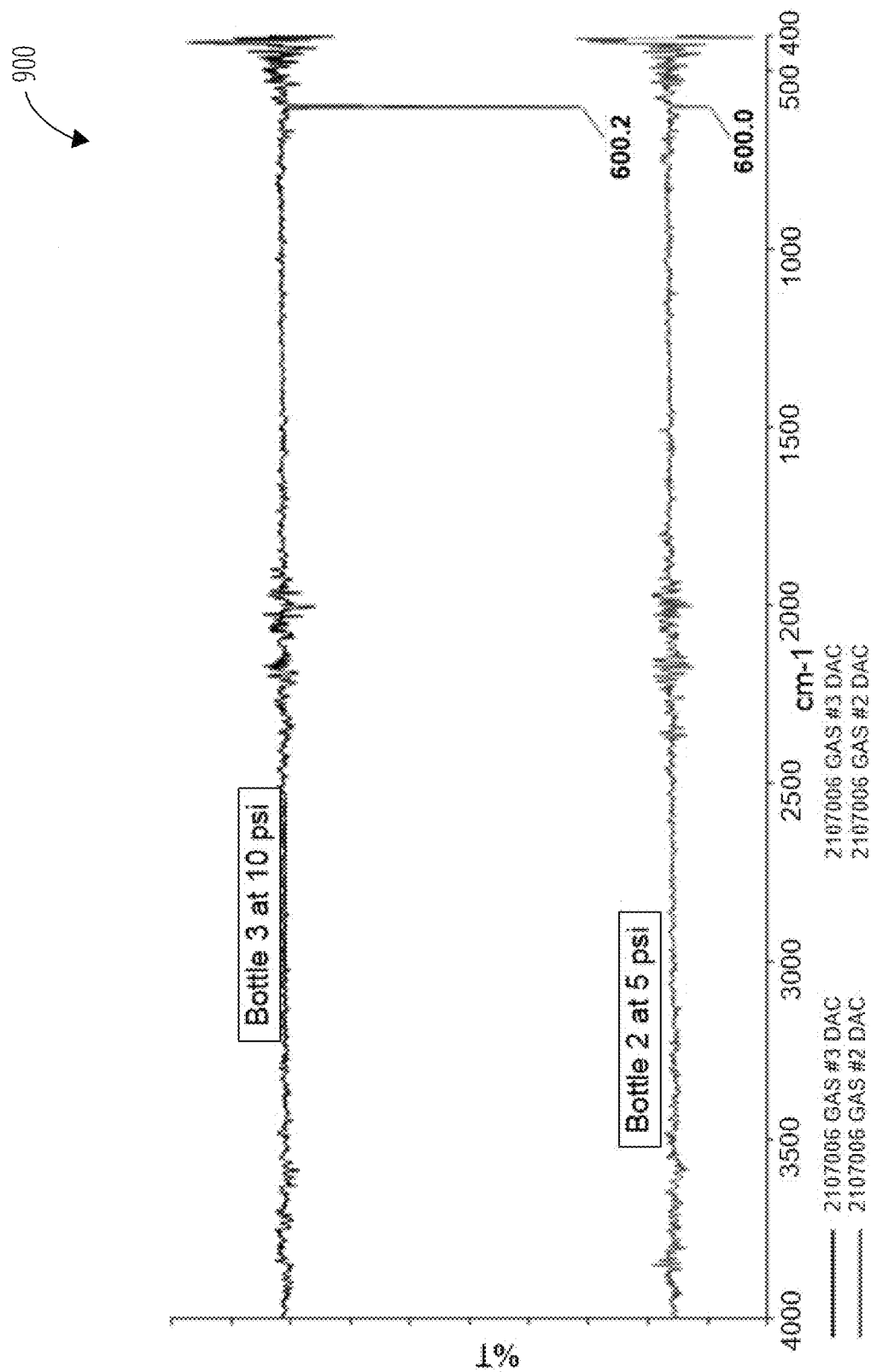
FIG. 9 shows plots 900 of FTIR molecular spectra of the structurally altered gas molecules.

FIG. 9 shows plots 900 of FTIR molecular spectra of the structurally altered gas molecule at pressures of 10 per square inch (psi) and 5 psi. The data on the gas according to the present disclosure shows a structural response at ~600 $cm^{-1}$ vs. percent transmittance % T indicating a change in structure. Regular water or divalent gases, (such as $H_2$ or $O_2$),— do not show any structural response in the FTIR 600 cm-1 range, and the 600 $cm^{-1}$ response observed here in the gas according to the present disclosure increases proportionally with pressure, thus reconfirming that the IR response data at ~600 $cm^{-1}$ is proportional and real.

The peaks at 600.2 $cm^{-1}$ and 600.0 $cm^{-1}$ in the plots 900 show that the structurally altered gas molecule 160 has a unique structure different from the structure of the pure water vapor. In comparison, an FTIR molecular spectra of the pure water vapor has no peaks in the area around 600 $cm^{-1}$. Additionally, the peaks at 600 $cm^{-1}$ cannot be related to a diatomic gas because the FTIR of divalent gases does not include peaks. Furthermore, the peaks at 600.2 $cm^{-1}$ and 600.0 $cm^{-1}$ are directly proportional to the observed gas molecule pressures recorded during the analysis. This proportionality substantiates that the peaks at 600.2 $cm^{-1}$ and 600.0 $cm^{-1}$ are caused by the pure structurally altered gas molecule 160 generated by system 202.

Figure 10:
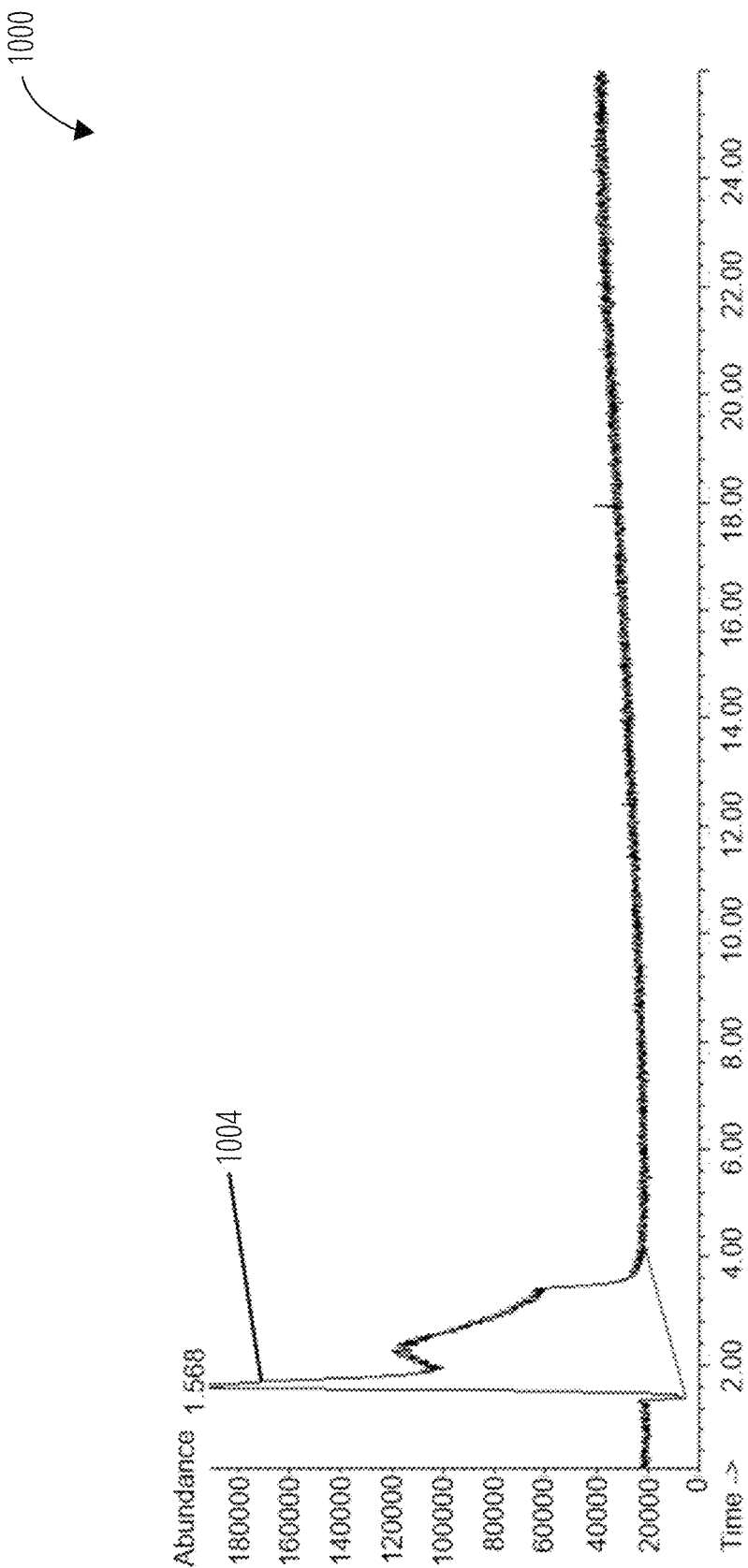
FIG. 10 shows a plot of gas chromatography—mass spectrometry (GCMS) measurements of peaks of regular water.

FIG. 10 shows plot 1000 of gas chromatography—mass spectrometry (GCMS) measurements of peaks of regular water 1004.

Figure 11:
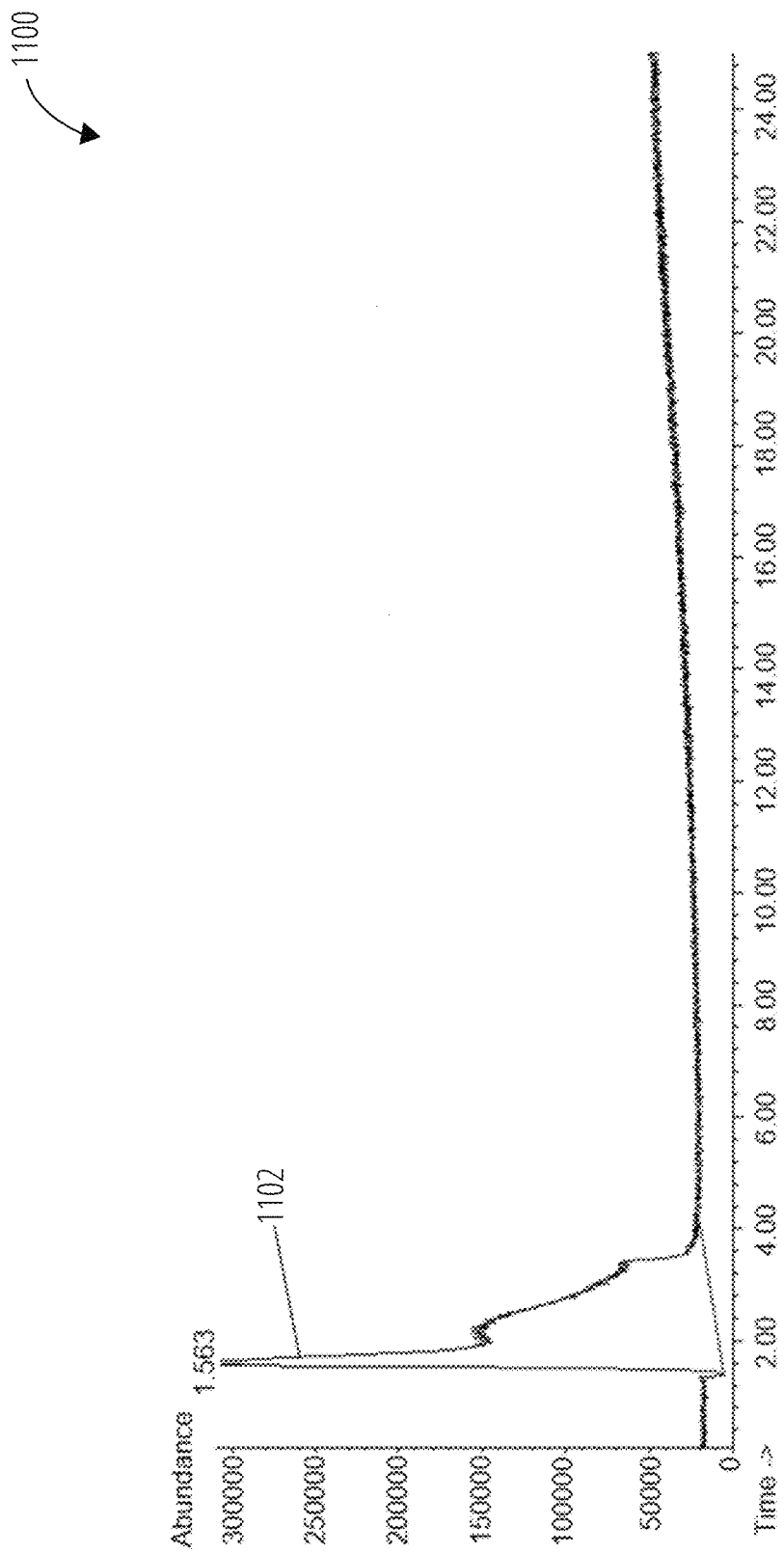
FIG. 11 shows a plot of gas chromatography—mass spectrometry (GCMS) measurements of peaks of gas infused water.

FIG. 11 shows a plot 1100 of gas chromatography—mass spectrometry (GCMS) measurements of peaks of gas infused water 1102.

The first peak in the 1.56 range on the X axis (Time) shows an approximate 40% increase in value of Abundance, (Y axis) from 200,000 to 320,000 or ~37.5% in the chromatogram 610 (WA—water after infusion with the structurally altered gas molecule 160) as compared to the chromatogram 620 (WB—the water before the infusion). The second peak in the 2.20 range on the X axis (Time) shows an increase in Abundance, (Y Axis) from 120,000 for WB to 155,000 for WA or ~22.6%. These differences indicate structural change of the water treated by the structurally altered gas molecule. Specifically, the differences indicate differences in H—O bond length, H—O—H bond angle, and decreasing influence of hydrogen bond with the increase in vapor release in the GC-MS sample chamber.

Data in FIG. 10 and FIG. 11 indicates a significant increase in the abundance (20K to 32K) at the ~1.56 time interval vs as well as the total abundance under the curve. This increase is directly proportional to the increase of abundance of the gas in the water treated with the gas according to the present disclosure.

The measured and observed changes in the molecular structure of the gas in FIG. 10 and FIG. 11 enable it to possess non-polar behavior and accommodate more efficient electron sharing as MOT states.

Figure 12:
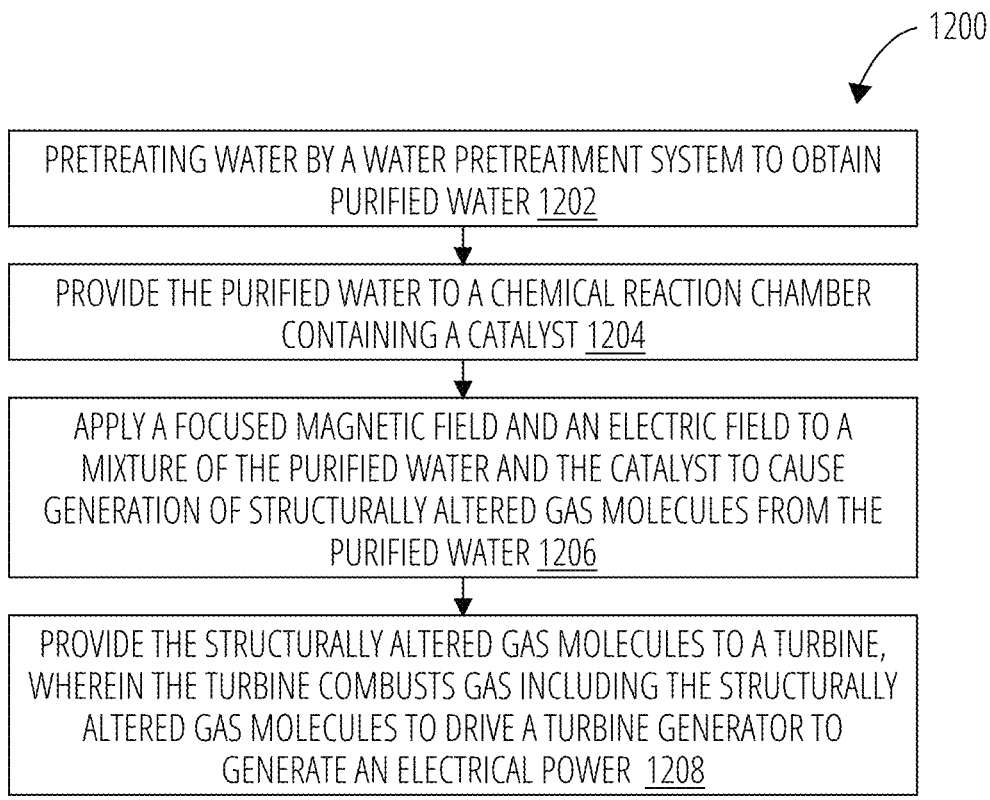
FIG. 12 is a flow chart illustrating a method for generating power, according to an example embodiment.

FIG. 12 is a flow chart of method 1200 for generating power, according to an example embodiment. In some embodiments, the operations of method 1200 may be combined, performed in parallel, or performed in a different order. The method 1200 may also include additional or fewer operations than those illustrated.

In block 1202, method 1200 may include pretreating water by a water pretreatment system to obtain purified water. The water pretreatment system can be powered by a wind power generator or a solar power generator.

In block 1204, method 1200 may include providing purified water to a chemical reaction chamber containing a catalyst.

In block 1206, method 1200 may include applying a focused magnetic field and an electric field to a mixture of the purified water and the catalyst to cause generation of structurally altered gas molecules from the purified water. The focused magnetic field is generated by a magnetic field generator. The electric field can be generated by an electric field generator. The electric field generator is powered by an electric power bank. The electric power bank may store power produced by one or more of the following: a wind power generator and a solar power generator.

The catalyst may include an electrolyte solution made using a mixture of a hydroxide salt and an acid salt. The structurally altered gas molecules are a combination of two parts hydrogen and one part oxygen. The structurally altered gas molecule has a hydrogen-oxygen-hydrogen bond angle between 94 degrees and 104 degrees and a hydrogen-oxygen bond length between 0.95 Angstrom and 1.3 Angstrom. The structurally altered gas molecules can be stable at a pressure exceeding 300 pounds per square inch gauge.

In block 1208, method 1200 may include providing the structurally altered gas molecules to a turbine, wherein the turbine combusts gas including the structurally altered gas molecules to drive a turbine generator to generate electrical power. Steam produced by the turbine can be provided to a condensing steam turbine designed to produce further electrical power. Condensed water produced by the condensing steam turbine can be provided to the chemical reaction chamber.

Thus, systems and methods for electrical power generation using structurally altered gas molecules derived from water have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:

1. A method for generating power, the method comprising:
   pretreating water by a water pretreatment system to obtain purified water;
   providing the purified water to a chemical reaction chamber containing a catalyst;
   applying a focused magnetic field and an electric field to a mixture of the purified water and the catalyst to cause generation of structurally altered gaseous water molecules from the purified water, wherein:

the structurally altered gaseous water molecules are a combination of two parts hydrogen and one part oxygen; and the structurally altered gaseous water molecules have a hydrogen-oxygen-hydrogen bond angle between 94 degrees and 104 degrees and a hydrogen-oxygen bond length between 0.95 Angstrom and 1.3 Angstrom; and providing the structurally altered gaseous water molecules to a turbine, wherein the turbine combusts gas including the structurally altered gaseous water molecules to drive a turbine generator to generate an electrical power.

2. The method of claim 1, wherein the focused magnetic field is generated by a magnetic field generator.

3. The method of claim 1, wherein the electric field is generated by an electric field generator.

4. The method of claim 3, wherein the electric field generator is powered by an electric power bank.

5. The method of claim 4, wherein the electric power bank stores power produced by one or more of the following: a wind power generator and a solar power generator.

6. The method of claim 1, wherein steam produced by the turbine is provided to a condensing steam turbine designed to produce further electrical power.

7. The method of claim 1, wherein condensed water produced by the condensing steam turbine is provided to the chemical reaction chamber.

8. The method of claim 1, wherein the water pretreatment system is powered by one or more of the following: a wind power generator and a solar power generator.

9. The method of claim 1, wherein the structurally altered gaseous water molecules are stable at a pressure exceeding 300 pounds per square inch gauge.

10. The method of claim 1, wherein the catalyst includes an electrolyte solution made using a mixture of a hydroxide salt and an acid salt.

11. A system for generating power, the system comprising:

a water pretreatment system for pretreating water by to obtain purified water;

a chemical reaction chamber for mixing a catalyst and the purified water;

an electric field generator and a magnetic field generator for applying a focused magnetic field and an electric field to a mixture of the purified water and the catalyst to cause generation of structurally altered gas molecules from the purified water, wherein:

the structurally altered gas molecules are a combination of two parts hydrogen and one part oxygen; and the structurally altered gas molecule has a hydrogen-oxygen-hydrogen bond angle between 94 degrees and 104 degrees and a hydrogen-oxygen bond length between 0.95 Angstrom and 1.3 Angstrom; and a turbine to combust gas including the structurally altered gas molecules to drive a turbine generator to generate an electrical power.

12. The system of claim 11, wherein the magnetic field generator includes one of the following: earth magnets, solenoids, and electromagnets.

13. The system of claim 11, wherein the electric field generator is powered by an electric power bank.

14. The system of claim 13, wherein the electric power bank stores power produced by a wind power generator.

15. The system of claim 13, wherein the electric power bank stores power produced by a solar power generator.

16. The system of claim 11, wherein steam produced by the turbine is provided to a condensing steam turbine designed to produce further electrical power.

17. The system of claim 11, wherein condensed water produced by the condensing steam turbine is provided to the chemical reaction chamber.

18. The system of claim 11, wherein the water pretreatment system is powered by one or more of the following: a wind power generator and a solar power generator.

19. The system of claim 11, wherein the structurally altered gas molecules are stable at a pressure exceeding 300 pounds per square inch gauge.

20. The system of claim 11, wherein the catalyst includes an electrolyte solution made using a mixture of a hydroxide salt and an acid salt.

* * * * *